(12) United States Patent
Kousai et al.

(10) Patent No.: US 8,376,962 B2
(45) Date of Patent: Feb. 19, 2013

(54) GUIDE WIRE

(75) Inventors: Tadashi Kousai, Glasgow (GB);
Akihiko Umeno, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 303 days.

(21) Appl. No.: 12/720,612

(22) Filed: Mar. 9, 2010

(65) Prior Publication Data

US 2010/0228229 A1 Sep. 9, 2010

Related U.S. Application Data

(60) Provisional application No. 61/159,508, filed on Mar. 12, 2009.

(30) Foreign Application Priority Data

Mar. 9, 2009 (JP) .................................. 2009-055453

(51) Int. Cl.
*A61B 5/00* (2006.01)
(52) U.S. Cl. ........................................................ 600/585
(58) Field of Classification Search .................... 600/585
See application file for complete search history.

(56) References Cited

U.S. PATENT DOCUMENTS

| | | | | |
|---|---|---|---|---|
| 5,107,852 A * | 4/1992 | Davidson et al. | ............. | 600/585 |
| 5,379,779 A | 1/1995 | Rowland et al. | | |
| 6,329,069 B1 * | 12/2001 | Azizi et al. | ..................... | 428/600 |
| 7,014,616 B2 * | 3/2006 | Ferrera | .......................... | 600/585 |
| 2004/0167438 A1 * | 8/2004 | Sharrow | ......................... | 600/585 |
| 2006/0047224 A1 * | 3/2006 | Grandfield | ..................... | 600/585 |
| 2007/0096357 A1 | 5/2007 | Yamada et al. | | |
| 2007/0178131 A1 * | 8/2007 | Yamada et al. | ............... | 424/423 |
| 2008/0281230 A1 * | 11/2008 | Kinoshita et al. | ............. | 600/585 |

FOREIGN PATENT DOCUMENTS

| | | |
|---|---|---|
| EP | 0982046 A1 | 3/2000 |
| EP | 1875941 A1 | 1/2008 |
| JP | 2004-008653 A | 1/2004 |
| JP | 2004-041254 A | 2/2004 |
| JP | 2005-205183 A | 8/2005 |
| WO | WO 2008/097359 A1 | 8/2008 |

OTHER PUBLICATIONS

Partial European Search Report dated Jul. 6, 2010 issued in the corresponding European Patent Application No. 10155749.

* cited by examiner

*Primary Examiner* — Max Hindenburg
(74) *Attorney, Agent, or Firm* — Buchanan Ingersoll & Rooney, P.C.

(57) ABSTRACT

A guide wire includes a core possessing a distal end part and a proximal end part, a distal covering layer covering the distal end part of the core, and a proximal covering layer covering the proximal end part of the core. The proximal covering layer includes a first layer that covers the surface of the core, and a second layer that partly covers the surface of the first layer. The first layer has a first part which is not covered by the second layer and a second part which is covered by the second layer, and the surface of the second part is tightly surrounded by the proximal end of the distal covering layer.

18 Claims, 4 Drawing Sheets

GUIDE WIRE

This application claims priority under 35 U.S.C. §119(e) with respect to U.S. Provisional Application No. 61/159,508 filed on Mar. 12, 2009, and also claims priority under 35 U.S.C. §119(a) with respect to Japanese Application No. 2009-055453 filed on Mar. 9, 2009, the entire content of both of which is incorporated herein by reference.

TECHNOLOGICAL FIELD

The present invention generally relates to a guide wire.

BACKGROUND DISCUSSION

For insertion of a catheter into a biological lumen such as digestive tract and blood vessel, a guide wire is employed to lead the catheter to a desired position in the lumen. When in use, the guide wire is passed through the catheter.

The guide wire is also employed to lead the catheter, which is inserted into an endoscope or its lumen, to a desired position of the biological lumen being observed or treated through the endoscope.

Among guide wires proposed so far is one disclosed in U.S. Pat. No. 5,379,779. The disclosed guide wire includes a core and a coating layer covering the surface thereof, the core having the main body and the distal end part extending from the main body. This guide wire has a heat-shrinkable tube of fluoroplastic resin as its coating layer which reduces frictional resistance and improves slidability, thereby making the guide wire easier to handle.

However, the guide wire mentioned above, which is covered with a heat-shrinkable tube as the coating layer, exhibits poor adhesion between the core and the heat-shrinkable tube. Thus, when the guide wire is turned in the presence of a comparatively large load, only the heat-shrinkable tube turns, and torque is not transmitted to the core. Moreover, the heat-shrinkable tube of fluoroplastic resin is comparatively expensive and is not so low in frictional resistance.

To address this problem, it has been proposed to form the covering layer mentioned above from a fluoroplastic resin. The resulting guide wire includes a core, a distal covering layer which covers the distal end part of the core and is formed from a flexible material, and a main body covering layer which covers the main body of the core and is formed from a fluoroplastic resin. The covering layers are formed such that the rear end of the distal covering layer overlaps the distal end of the main body covering layer, so that the core does not expose itself.

This guide wire construction exhibits poor adhesion between the distal covering layer and the main body covering layer and so the former easily peels off from the latter.

SUMMARY

A guide wire includes a core having a proximal end part and a distal end part extending from the proximal end part, a distal covering layer that covers the distal end part, and a proximal covering layer that covers the proximal end part. The proximal covering layer includes a first layer that covers the surface of the core and a second layer that partly covers the surface of the first layer. The first layer has a first part which is not covered by the second layer and a second part which is covered by the second layer, and the outer surface of the second part is tightly surrounded by the proximal end of the distal covering layer. The guide wire disclosed here is constructed such that the distal covering layer is not so susceptible to being peeled off.

The first layer is preferably configured so that the outer surface of the first part of the first layer exhibits stronger adhesive characteristics relative to material forming the second layer than the outer surface of the distal end portion of the first layer. The guide wire is preferably constructed so that the second layer adheres to the surface of the first part more strongly than the surface layer adheres to the surface of the second part.

The first layer is preferably configured so that the outer surface of the distal end portion of the first layer exhibits stronger adhesive characteristics relative to material forming the distal covering layer than the outer surface of the first part of the first layer. The guide wire is preferably constructed so that the distal covering layer adheres to the surface of the second part more strongly than the distal covering layer adheres to the surface of the first part. The second layer is preferably formed mainly from a fluoroplastic resin.

The first part of the first layer is preferably formed from a material containing a fluoroplastic resin and a curable resin, with the content of the fluoroplastic resin of the first part higher near the second layer than near the core. The fluoroplastic resin in the first part exists at least partly in the form of fine particles. The second part can be formed from a material containing a fluoroplastic resin and a curable resin, and the content of the fluoroplastic resin of the second part is lower near the surface of the second part than near the surface of the first part.

If fluoroplastic resin exists in the second part, the fluoroplastic resin exists at least partly in the form of fine particles. However, the second part can be formed from a resin material that contains no fluoroplastic resin. The distal covering layer is formed from a resin material which is more flexible than the second layer. The distal covering layer can have an outside diameter at the proximal end which is larger than that at the distal end of the second layer.

The distal covering layer can be configured so that the proximal end of the distal covering layer terminates beyond the distal end of the second layer. The proximal end of the distal covering layer can overlap with the surface of the second layer. The distal end of the second layer may be surface-treated for improving adhesion to the distal covering layer.

The guide wire disclosed here includes the proximal covering layer composed of a surface layer and an underlying layer, with the surface layer able to perform its intended function and the underlying layer able to perform another function. In other words, adhesion between the underlying layer and the distal covering layer is higher than that between the surface layer and the distal covering layer. Moreover, the proximal end of the distal covering layer tightly overlaps with the second part of the underlying layer. This helps prevent the proximal end of the distal covering layer from peeling off, and helps impart high reliability to the guide wire.

According to another aspect, a guide wire includes a core comprised of a main body and a distal end part, with the main body possessing a distal end and a proximal end, and the distal end part of the core extending in a fore direction from the distal end of the main body. In addition, a distal covering layer covers the distal end part of the core, and a main body covering layer covers the main body of the core. The main body covering layer comprises an underlying layer that covers the outer surface of the core and a surface layer that partly covers the outer surface of the underlying layer. The underlying layer includes a first part possessing an outer surface covered by the surface layer, and a second part possessing an outer surface not covered by the surface layer. The outer surface of the second part is surrounded by the proximal end portion of the distal covering layer which contacts the outer surface of the second part.

Another aspect disclosed here involves a method of fabricating a guide wire. The method includes applying coating solution in liquid form to the outer surface of a core, heating the coating solution after the coating solution is applied to the core to cause the resin in at least the first part of the coating solution to migrate towards an outer surface of the coating solution to produce a first part of an underlying layer in which a content of the resin adjacent an outer surface of the first part of the underlying layer is greater than a content of the resin adjacent the core, wherein the first part of the underlying layer possesses an outer surface. The coating solution applied to the core also produces a second part of the underlying layer that possesses an outer surface, with the second part of the underlying layer extending longitudinally in a fore direction from a distal end of the first part of the underlying layer, and with the underlying layer covering a main part of the core while leaving a distal end part of the core uncovered by the underlying layer. In addition, the method involves providing a surface layer on the first part of the underlying layer without providing the surface layer on the second part of the underlying layer, wherein the surface layer adheres to the outer surface of the first part of the underlying layer, and providing a distal covering layer on the distal end of the core, with the distal covering layer adhering to the outer surface of the first part of the underlying layer.

DETAILED DESCRIPTION

Figure 1:
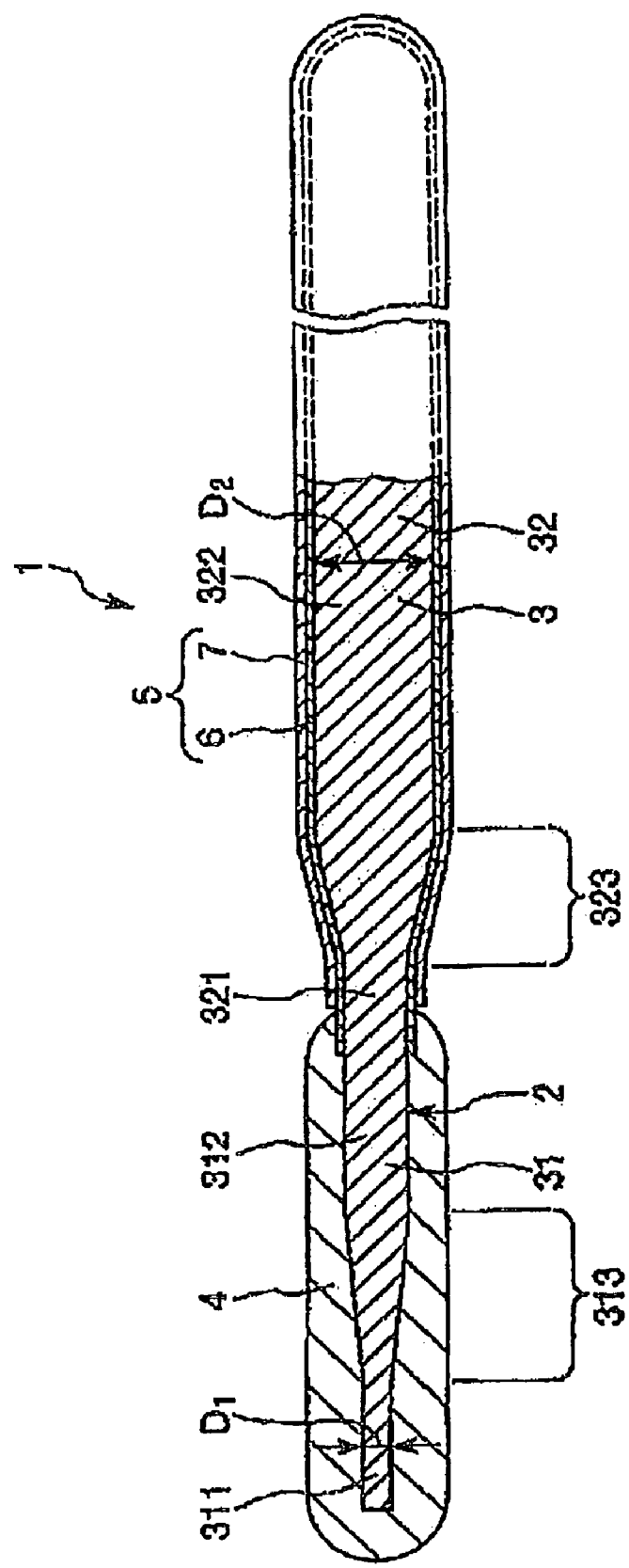
FIG. 1 is a longitudinal cross-sectional view of the guide wire according to one embodiment disclosed here.
Figure 2:
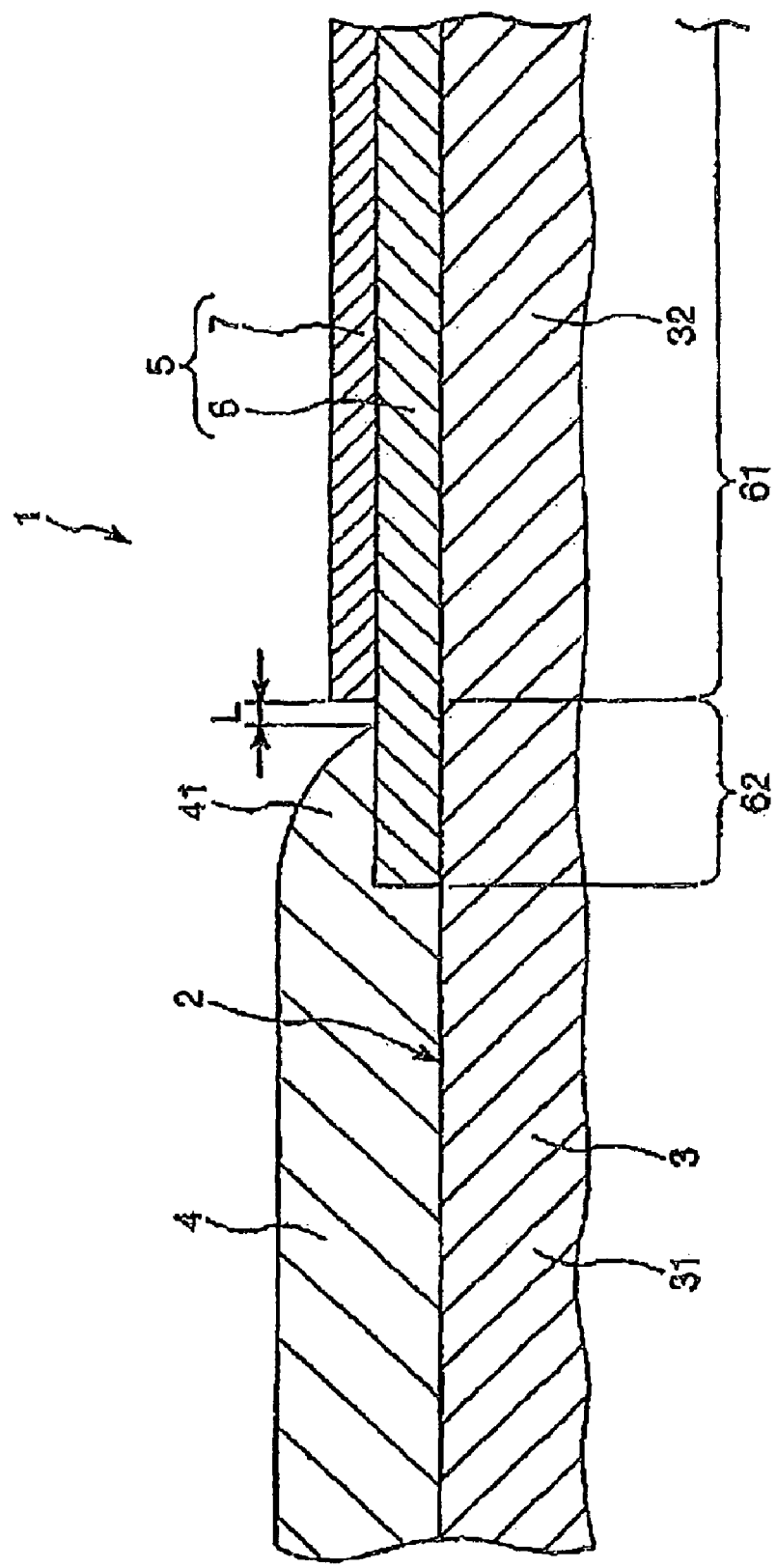
FIG. 2 is an enlarged longitudinal cross-sectional view of a portion of the guide wire shown in FIG. 1.

One embodiment of the guide wire disclosed here is illustrated in FIGS. 1 and 2. In the description which follows, the phrase "proximal end" refers to the right side in FIGS. 1 and 2, the phrase "distal end" refers to the left side in FIGS. 1 and 2, the term "up" refers to the upper side in FIG. 2, and the term "down" refers to the lower side in FIG. 2. The illustration in FIG. 1 is a somewhat schematic representation in which the length is reduced and the thickness increased or exaggerated for facilitating an understanding of aspects of the guide wire. Thus, the illustrated length-to-thickness ratio is not identical to the real or actual ratio.

The guide wire 1 shown in FIG. 1 is a guide wire configured to be inserted into the lumen of a medical tube such as a catheter and an endoscope. The guide wire includes a flexible core 3, a distal covering layer 4, and a proximal covering layer 5.

According to the embodiment disclosed here, the core 3 is a continuous wire (a wire integrally molded in one piece at the same time) and possesses a round (circular) cross section. However, the guide wire is not limited in that regard. The core 3 may be formed from a plurality of wires of identical or different materials which are welded or brazed together. Also, the core 3 may have additional constituents.

The overall length of the guide wire 1 is not limited to a specific length, though it is preferably about 200 to 5000 mm long. The guide wire 1 is also not limited to a specific outside diameter, but is preferably about 0.2 to 1.2 mm.

The core 3 extends over the entire length of the guide wire 1. The core 3 is made up of a distal end part 31 and a proximal end part 32 (i.e., a main body part). The distal end part 31 of the core wire corresponds to (is located at) the distal end of the guide wire 1. The proximal end part 32 of the core wire corresponds to the main body of the guide wire 1 and is provided at the proximal side of the distal end part 31.

According to the present embodiment, the distal end part 31 of the core 3 consists of two parts: one part having a constant outside diameter (constant outer diameter part) and another part which is a tapering part 313 having a varying outside diameter that tapers (becomes smaller) toward the distal end. The core 3 may have one or more than one tapering part. The illustrated core has one tapering part.

Owing to the tapering part 313, the core 3 gradually decreases in stiffness (flexural and torsional) toward the distal end of the core. Thus the guide wire 1 has good flexibility in its distal end part, and this helps the guide wire 1 to relatively safely advance through the blood vessel and also helps inhibit or prevent the guide wire from kinking The tapering part 313 has an angle of taper which may be constant or variable in the lengthwise direction of the guide wire 1. Also, steep and gentle tapers may be arranged alternately.

At distal the tip of the tapering part 313 of the distal end part 31 is the distal end thin part 311 which has a uniform outside diameter throughout its length up to its distal end. At the base of the tapering part 313 of the distal end part 31 is the distal end thick part 312 which has a uniform outside diameter throughout its length from the tapering part 313 up to the distal end of the proximal en part 32.

The distal end thin part 311, which extends in the distal or fore direction from the distal end of the tapering part 313 of the core 3, lengthens the flexible part of the distal end and hence makes the foremost part more flexible.

Moreover, the distal end thin part 311 of the core 3 may be at least partly reshapable. This reshapable part should preferably be flat or prismatic. Reshapeable refers to the ability of the distal end thin part 311 of the core 3 to be shaped to a desired shape, for example manually or through use of a mandrel or the like, and to retain that shape.

According to the present embodiment, the proximal end part 32 of the core 3 is comprised of two parts: one part (constant outer diameter part) having a constant outside diameter and another part which is a tapering part 323 having a varying outside diameter that tapers (becomes smaller) toward the distal end, as in the case of the distal end part 31 mentioned above. The proximal end part 32 of the core 3 may have one or more than one tapering parts. The illustrated proximal end part (main body) 32 of the core 3 has one tapering part. The tapering part 323 has an angle of taper which may be constant or variable in the lengthwise direction of the guide wire 1. For example, the tapering part can be configured to include steep and gentle tapers arranged alternately.

At the distal end of the tapering part 323 of the proximal part 32 is the main body thin part 321 which has a uniform outside diameter throughout its length from the distal end of the main body tapering part 323 up to the proximal end of the distal end part 31, with the outside diameter being equal to that of the proximal end of the distal end part 31. At the proximal side of the tapering part 323 of the proximal end part 32 is the main body thick part 322 which has a uniform outside diameter throughout its length up to the proximal end of the guide wire.

The outside diameter of the main body thick part 322 of the proximal part 32 is not limited to a specific diameter. The outside diameter D2 of the main body thick part 322 should preferably be about 0.3 to 1.0 mm, more preferably about 0.4 to 0.7 mm.

The outside diameter of the distal end thin part 311 of the distal end part 31 is not limited to a specific value. As an example though, the outside diameter D1 of the distal end thin part 311 is preferably about 0.05 to 0.3 mm, more preferably about 0.1 to 0.2 mm. The outside diameter of the distal end thin part 311 may be constant or tapered (narrowed) toward the distal end.

The length of the distal end thin part 311 is not limited; but should preferably be about 0 to 100 mm, more preferably about 10 to 50 mm.

The raw material from which the core 3 is fabricated includes superelastic alloys such as stainless steel, Ni Ti alloy, Ni Al alloy, and Cu Zn alloy and other metallic materials, and comparatively stiff plastic materials. These materials may be used alone or in combination with one another.

In addition, the guide wire 1 has the distal covering layer 4 which covers and firmly adheres to the surface of the distal end part 31 or the outer surface of the core 3.

The distal covering layer 4 is formed with various purposes in mind. For example, the distal covering layer 4 helps ensure safety for the guide wire 1 inserted into a blood vessel. For this purpose, the distal covering layer 4 should be formed from a flexible material, preferably one which is more flexible than the material forming the surface layer 7 described later.

Examples of such flexible materials for the distal covering layer 4 include polyolefins such as polyethylene and polypropylene, polyvinyl chloride, polyester such as PET (polyethylene terephthalate) and PBT (polybutylene terephthalate), polyamide, polyimide, polyurethane, polystyrene, silicone resin, thermoplastic elastomers such as polyurethane elastomer, polyester elastomer, and polyamide elastomer, rubbery materials such as latex rubber and silicone rubber, and their composite materials.

The distal covering layer 4 formed from any of the thermoplastic elastomers or rubbery materials mentioned above imparts good flexibility to the distal end of the guide wire 1, assuredly inhibiting or preventing blood vessels from being cut, so that it imparts greater safety to the guide wire 1 being inserted into a blood vessel.

The distal covering layer 4 should preferably be incorporated with particles (filler) of X-ray opaque material (or contrast medium), so that the guide wire 1 can be smoothly inserted into a living body with the help of X ray radioscopy to indicate the position of the distal end.

The above-mentioned particles may be formed from any material so long as it is opaque to X rays. Such materials include, for example, gold, platinum, and tungsten, and their alloys (such as platinum-iridium alloy).

The thickness of the distal covering layer 4 is not limited to a particular thickness, but should be properly established according to the object, material, and shape of the distal covering layer 4. It is usually about 100 to 500 μm, preferably about 150 to 350 μm (on average). An excessively small thickness does not allow the distal covering layer 4 to achieve its objective. A distal covering layer 4 with an excessively large thickness adversely affects the physical properties of the guide wire 1.

The distal covering layer 4 may be of laminate structure comprised of more than one layer.

Also, the guide wire 1 has the proximal covering layer 5 (i.e., main body covering member) which covers and tightly adheres to the periphery or outer surface of the proximal part 32 of the core 3.

The proximal covering layer 5 includes the underlying layer or first layer 6 which covers (contacts) the surface of the core 3 and the surface layer or second layer 7 which covers (contacts) the underlying layer 6 (first layer). In this illustrated embodiment, the proximal covering layer 5 includes only the underlying layer 6 (firs layer) and the surface layer 7 (second layer). The outer surface of the distal end of the underlying layer 6 is not covered by the surface layer 7 so that the underlying layer 6 extends further in the distal direction than the surface layer 7 such that the distal end portion of the first layer 6 extends distally beyond the distal-most end of the second layer 7. In other words, the underlying layer 6 consists of a first part 61 which is covered by the surface layer 7 and a second part 62 (distal end portion of the underlying layer 6) which is not covered by the surface layer 7. The underlying layer 6 tightly adheres to the outer surface of the proximal end part 32 of the core 3, and the surface layer 7 tightly adheres to the outer surface of the underlying layer 6. The underlying layer 6 may tightly adhere to the outer surface of the proximal end part of the distal end thick part 312. Alternatively, the distal covering layer 4 may tightly adhere to the outer surface of the distal end part of the main body thin part 321.

The underlying layer 6 and the surface layer 7 should preferably be formed as coating layers such as a coating layer formed by applying a liquid material to produce a coating film and then heating the resultant coating film. This helps make the proximal covering layer 5 adhere to the core 3 more strongly than a heat-shrinkable tube. The relatively strong adhesion helps facilitate good torque transmission characteristics for the core 3 when the guide wire is twisted. Moreover, the foregoing process provides the proximal covering layer 5 which is thinner than a heat-shrinkable tube. The result is that the guide wire can be configured to possess an outside diameter the same as other guide wires having a different main body covering layer, yet with a thicker (larger diameter) core 3 and hence stiffer core.

The surface layer 7 of the proximal covering layer 5 may be formed for various purposes, such as reducing the friction (slide resistance) of the guide wire 1, which makes the guide wire 1 easier to operate.

To realize this purpose, the surface layer 7 should preferably be formed from any material that reduces friction (first resin). The guide wire 1 with reduced friction against the lumen of the catheter can be handled relatively easily. Moreover, it is free from kinking and distortion when it is moved or twisted in the catheter.

Those materials capable of reducing friction include, for example, polyolefins such as polyethylene and polypropylene, polyvinyl chloride, polyester such as PET and PBT, polyamide, polyimide, polyurethane, polystyrene, polycarbonate, silicone resin, fluoroplastics such as PTFE, ETFE, and PFA, and their composite materials.

Of these examples, fluoroplastics (and composite materials thereof) are most desirable. In other words, the surface layer 7 should preferably be formed from a material composed mainly of fluoroplastic resin. That is, the material forming the surface layer 7 preferably contains more fluoroplastic resin, by weight, than all other materials combined (i.e., the surface layer 7 comprises more than 50 wt % fluoroplastic resin). This resin will effectively reduce friction between the guide wire 1 and the inside of the catheter, thereby making the guide wire 1 slide more smoothly for easier operation without significant kinking and distortion during movement or twisting.

In the following further description of this embodiment and the second and third embodiments mentioned later, it is assumed that the surface layer 7 is formed from a fluoroplastic resin.

The outer surface of the second part 62 of the underlying layer 6 is tightly covered with the proximal end part 41 of the distal covering layer 4, so that the outer periphery of the core 3 is entirely covered with the distal covering layer 4 and the proximal covering layer 5, and so the core 3 is electrically insulated from outside. High electrical insulation permits the guide wire 1 to be used safely for an endoscope in conjunction with a high-frequency treating machine.

According to the present embodiment, the proximal end 41 of the distal covering layer 4 does not cover the surface of the second part 62 entirely but only partly. Thus, the proximal end tip of the distal covering layer 4 terminates at a position spaced from the distal end of the surface layer 7. In other words, there is a certain space or gap L separating the proximal end tip (proximal-most end) of the distal covering layer 4 and the distal end tip (distal-most end) of the surface layer 7 from each other.

The fact that the proximal end 41 of the distal covering layer 4 does not contact and does not overlap with the surface layer 7 makes it possible to reduce difference in outside diameter between the distal covering layer 4 and the proximal covering layer 5. It is desirable that the proximal end of the distal covering layer 4 should be larger in outside diameter than the distal end of the surface layer 7.

The underlying layer 6 also functions as an adhesive to bond together the core 3 and the surface layer 7. It should preferably be formed from a material containing a thermosetting resin and a fluoroplastic resin (first resin). Although fluoroplastic resins are usually poor in adhesion to other materials, the fluoroplastic resin contained in the underlying layer 6 improves adhesion to the surface layer 7, and the thermoplastic resin contained in the underlying layer 6 increases adhesion between the core 3 and the underlying layer 6 and adhesion between the distal covering layer 4 and the underlying layer 6. Thus, the distal covering layer 4 and the proximal covering layer 5 firmly adhere to the core 3.

The fact that there is no contact between the proximal end 41 of the distal covering layer 4 and the surface layer 7 formed from a fluoroplastic resin helps inhibit a decrease in adhesion between the proximal end 41 of the distal covering layer 4 and the distal end of the proximal covering layer 5, and also helps prevent these layers from delaminating.

The thermosetting resin constituting the underlying layer 6 includes, for example, epoxy resin, phenolic resin, polyester (unsaturated polyester), polyimide, silicone resin, and polyurethane. They may be used alone or in combination with one another.

If the surface layer 7 is formed mainly from a fluoroplastic resin, other materials used with the fluoroplastic resin to constitute the underlying layer 6 should preferably be those which withstand the sintering temperature of the fluoroplastic resin. Examples of materials to be used with fluoroplastic resin for the underlying layer 6 include polysulphone, polyimide, polyether ether ketone, polyarylene ketone, polyphenylene sulfide, polyarylene sulfide, polyamideimide, polyether imide, polyimidesulfone, polyarylsulfone, polyarylethersulfone, polyester, and polyethersulfone. They may be used alone or in combination with one another.

The content of the fluoroplastic resin in the underlying layer 6 should be about 20 to 80 wt %, preferably about 30 to 70 wt %, of the total amount of the underlying layer 6.

The content of the fluoroplastic resin in the underlying layer 6 may be uniform throughout the underlying layer 6. However, it should preferably be varied in such a way that the content of the fluoroplastic resin increases from the inside (close to the core 3) to the outside (close to the surface layer 7). This helps improve adhesion between the underlying layer 6 and the surface layer 7 and adhesion between the underlying layer 6 and the core 3. With this configuration, the content (wt %) of the fluoroplastic resin in a portion of the underlying layer 6 closer to the core 3 is less than the content (wt %) of the fluoroplastic resin in a portion (outermost portion) of the underlying layer 6 closer to the surface layer 7.

The content of the fluoroplastic resin in that part of the underlying layer 6 which is close to the core 3 should be about 10 to 50 wt %, preferably 10 to 30 wt %.

Also, the content of the fluoroplastic resin in that part of the underlying layer 6 which is close to the surface layer 7 should be about 50 to 80 wt %, preferably 60 to 80 wt %.

The underlying layer 6 mentioned above may be formed in any suitable manner, and is not limited to a specific manufacturing method. An example of a forming method is discussed below.

First, a coating solution for the underlying layer is prepared by mixing together a precursor of the thermosetting resin and the fluoroplastic resin in fine powder form. This coating solution is applied, in liquid form, to the outer surface of the core 3, followed by heating at a prescribed temperature. During heating, the fluoroplastic resin migrates to the surface side of the underlying layer 6 and the thermosetting resin cures. In this way, the underlying layer 6 is obtained in which the content of the fluoroplastic resin increases in a direction from that part close to the core 3 to that part close to the surface layer 7.

The heating temperature and time may vary depending on the kind of thermosetting resin and fluoroplastic resin and other conditions. Heating at about 170 to 220° C. for 10 to 60 minutes is preferable, and heating at about 180 to 210° C. for 30 to 60 minutes is more preferable. After the underlying layer 6 is applied to the surface of the proximal part 32 and dried, the distal covering layer 4 and the surface layer 7 are suitably applied. For example, following the application and drying of the underlying layer 6, the surface layer 7 can be applied to the underlying layer 6, and dried. Then, both the underlying layer 6 and the surface layer 7 can be sintered by heating. Thereafter, the distal covering layer 4 can be applied to the distal end part 31 and dried.

The fluoroplastic resin for the underlying layer 6 may be entirely or partly in the form of fine particles or in any other forms.

The thickness of the proximal covering layer 5 is not specifically limited. It should have an adequate thickness according to its objective, material, and forming method, preferably ranging from about 1 to 100 μm, more preferably from about 1 to 30 μm. The proximal covering layer 5 with an excessively small thickness may have difficulty achieving its objective or may be liable to peeling. Conversely, the proximal covering layer 5 with an excessively large thickness may adversely affect the physical properties of the guide wire 1 and may be susceptible to peeling.

The thickness of the underlying layer 6 and the surface layer 7, and the ratio of the thickness of the two layers 6, 7, are not limited to specific values. Usually, the thickness of the underlying layer 6 should be about 1 to 20 μm, preferably about 3 to 10 μm, and the thickness of the surface layer 7 should be about 1 to 20 μm, preferably about 3 to 10 μm.

One or both of the underlying layer 6 and the surface layer 7 may be a laminate structure composed of two or more layers.

The length of the second part 62 of the underlying layer 6 in the lengthwise direction of the guide wire 1 is not limited to a specific dimension. It is usually about 5 to 30 mm long, preferably about 5 to 20 mm long.

The length L of the space between the proximal end tip of the distal covering layer 4 and the distal end tip of the surface layer 7 is not specifically limited. It should be about 1 to 20 μm, preferably about 1 to 10 μm.

In addition, the guide wire 1 should have at least the outer surface of the distal end coated with a hydrophilic material which provides lubricity upon wetting, to reduce friction and improve slidability. This makes the guide wire 1 easier to operate.

Examples of the hydrophilic materials include cellulosic polymer, polyethylene oxide polymer, maleic anhydride polymer (such as methyl vinyl ether-maleic anhydride copolymer), acrylamide polymer (such as polyacrylamide, polyglycidyl methacrylate-dimethyl acrylamide (PGMA-DMAA) block copolymer), water-soluble nylon, polyvinyl alcohol, and polyvinyl pyrrolidone.

Such hydrophilic materials as mentioned above usually exhibit lubricity upon wetting, thereby reducing friction between the guide wire 1 and the inside wall of the catheter. Thus the guide wire 1 slides more easily and becomes easier to handle in the catheter.

The guide wire 1 mentioned above is constructed such that the proximal end part 41 of the distal covering layer 4 does not adhere to the layer 7 (surface of the underlying layer or second layer 7), but tightly adheres to the second part 62 of the underlying layer 6 (outer surface of the second part 62 of the underlying layer or first layer 6). This structure helps ensure adhesion for the proximal end part 41 and makes the guide wire 1 more reliable.

The guide wire disclosed here may be modified such that the proximal end part 41 of the distal covering layer 4 covers the entire outer surface of the second part 62.

Also, the guide wire disclosed here may be modified such that the proximal end part of the distal covering layer 4 is in contact with or tightly adheres to the distal end of the surface layer 7.

Figure 3:
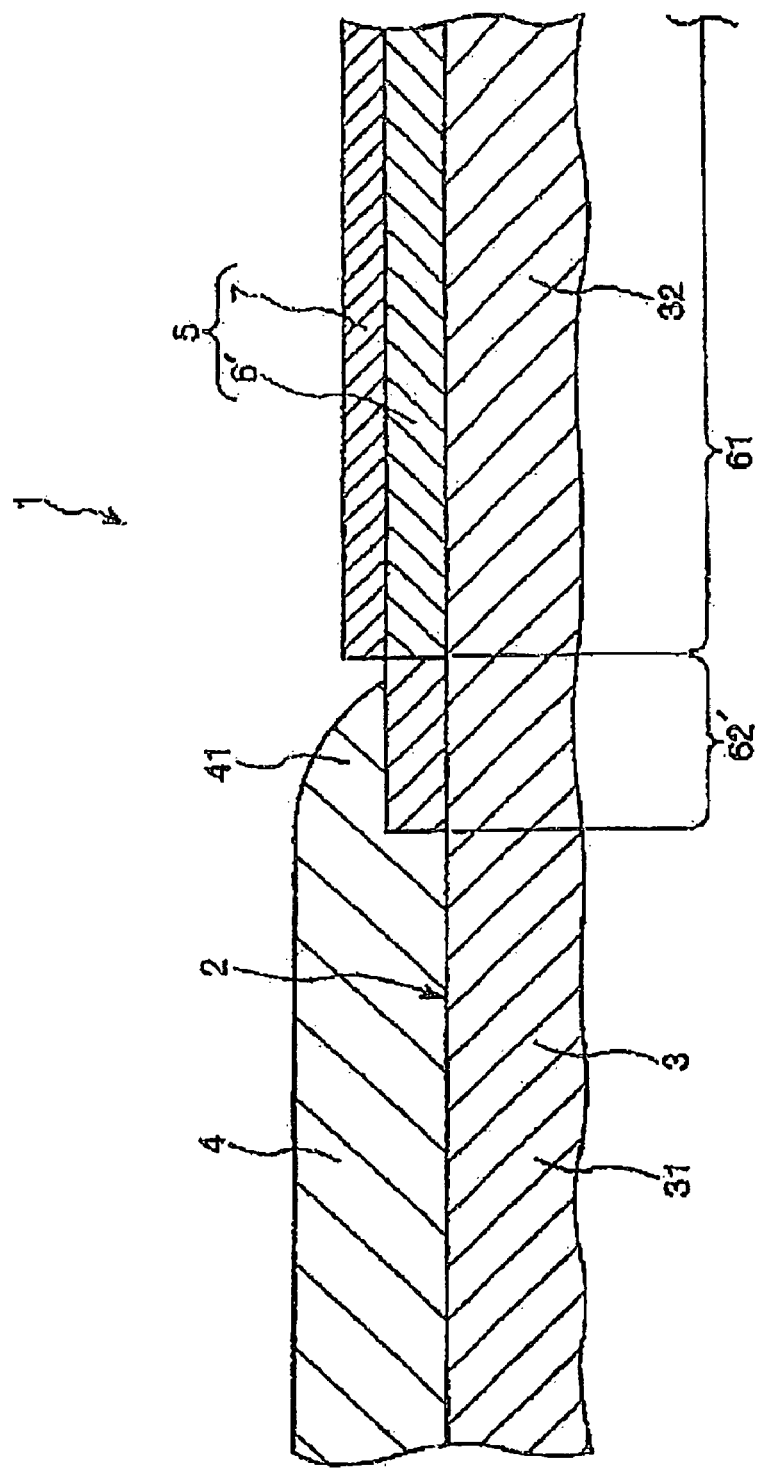
FIG. 3 is an enlarged longitudinal cross-sectional view of a portion of a guide wire according to a second embodiment disclosed here.

FIG. 3 illustrates a second embodiment of the guide wire. In the following description of this embodiment, the phrase "proximal end" refers to the right side in FIG. 3, the phrase "distal end" refers to the left side in FIG. 3, the term "up" refers to the upper side in FIG. 3, and the term "down" refers to the lower side in FIG. 3.

The description below primarily describes differences between this second embodiment of the guide wire and the first embodiment described above. Features in this second embodiment which are the same as those described above are identified by a common reference numeral and a description of such features is not repeated.

The second embodiment of the guide wire is identical to the first embodiment, except for the structure of the underlying layer or first layer 6'.

In the second embodiment of the guide wire shown in FIG. 3, the first part 61 of the underlying layer 6' is identical to that in the guide wire 1 of the first embodiment, but the second part 62' differs in its adhesion characteristics.

The first part 61 is composed of a thermosetting resin and a material containing a fluoroplastic resin, such that the content of the fluoroplastic resin increases from the core 3 to the surface layer 7 (from the core 3 toward the outer surface of the first part 61). On the other hand, the second part 62 is constructed in either of the following two ways (Structure 1 or Structure 2).

(Structure 1)

The second part 62' is composed of a thermosetting resin and a material containing a fluoroplastic resin, such that the content of the fluoroplastic resin at the portion of the second part 62' adjacent the outer surface (the portion adjacent the distal covering layer 4) is lower than the content of the fluoroplastic resin at the portion of the first part 61 adjacent to the surface layer 7. In other words, the outermost portion of the first part 61 adjoining the surface layer 7 has a higher content of the fluoroplastic resin than the outermost portion of the second part 62' adjoining the distal covering layer 4. This construction increases adhesion between the second part 62' and the distal covering layer 4. The content of the fluoroplastic resin in the second part 62' may be uniform throughout or gradually increasing or decreasing toward the outer surface from the core 3.

(Structure 2)

According to an alternative structure, the second part 62' is formed from a resin such as thermosetting resin free of fluoroplastic resin. This structure improves adhesion between the second part 62' and the distal covering layer 4 and adhesion between the second part 62' and the core 3. The thermosetting resin may be the same one as used for the underlying layer 6 in the first embodiment.

The first part 61 and the second part 62' of the underlying layer 6' adhere to the distal covering layer 4 and the surface layer 7 respectively in the following manner.

The first part 61 and second part 62' of the underlying layer 6' are configured (e.g., are comprised of material compositions) such that the outer surface of the second part 62' of the underlying layer 6' adheres more strongly to the material forming the distal covering layer 4 than the outer surface of the first part 61 of the underlying layer 6'. In other words, if the first part 61 of the underlying layer 6' was adhered to the distal covering layer 4, that adhesion would not be as strong as the adhesion between the outer surface of the second part 62' of the underlying layer 6' and the distal covering layer 4. This helps ensure a desired degree of adhesion between the second part 62' and the distal covering layer 4.

Also, the first part 61 and second part 62' of the underlying layer 6' are configured (e.g., are comprised of material compositions) such that the outer surface of the first part 61 of the underlying layer 6' adheres more strongly to the material forming the surface layer 7 than the outer surface of the second part 62' of the underlying layer 6'. In other words, if the second part 62' of the underlying layer 6' was adhered to the surface layer 7, that adhesion would not be as strong as the adhesion between the outer surface of the first part 61 of the underlying layer 6' and the surface layer 7. This helps ensure a desired degree of adhesion between the first part 61 and the surface layer 7.

The underlying layer 6' can be formed in any appropriate manner. As an example, in the case of Structure 1 described above, the underlying layer 6' is formed in the following manner.

First, a coating solution for the underlying layer is prepared by mixing together a precursor of the thermosetting resin and the fluoroplastic resin in fine powder form. This coating solution is applied to the surface of the core 3. The part corresponding to the first part 61 is heated at a first temperature, and the part corresponding to the second part 62' is heated at a second temperature which is lower than the first temperature.

The result of this procedure is that the fluoroplastic resin migrates toward the outer surface side of the underlying layer 6' at the part corresponding to the first part 61. With the thermosetting resin cured, the content of the fluoroplastic resin in the underlying layer 6' increases from the core 3 to the surface layer 7.

On the other hand, the thermosetting resin cures in that part corresponding to the second part 62', thereby forming the underlying layer 6'. Since the part corresponding to the second part 62' is heated at the second temperature which is lower than the first temperature, migration of the fluoroplastic resin takes place to a smaller extent (in Structure 1), and the underlying layer 6' is formed in which the content of the fluoroplastic resin increases from the core 3 to the surface layer 7, though to a lesser extent than in the first part 61. It is possible to heat the second part 62' at a second temperature which is sufficiently lower than the first temperature that migration of the fluoroplastic resin does not take place at all. In that alternative, the underlying layer 6' is formed such that the content of the fluoroplastic resin is uniform (inclusive of generally uniform) throughout. In any case, the content of the fluoroplastic resin at the portion of the second part 62' adjacent to the distal covering layer 4 is lower than the content of the fluoroplastic resin at the corresponding or same portion of the first part 61 adjacent the surface layer 7.

The first and second temperatures may be properly established according to the kinds and conditions of the thermosetting resin and fluoroplastic resin to be used. The first temperature should be about 170 to 220° C. for 10 to 60 minutes, preferably about 180 to 210° C. for 30 to 60 minutes. The second temperature should be about 130 to 180° C. for 3 to 15 minutes, preferably about 150 to 180° C. for 3 to 10 minutes. The temperatures refer to the surrounding temperature of the environment in which the parts are placed. For example, the first part may be arranged between heaters that make partial irradiation possible.

The fluoroplastic resin in the first part 61 exists in the form of fine particles when it is heated at the first temperature, and the fine particles expose themselves at the outer surface of the first part 61. After that, when the surface 7 is formed from a material composed mainly of a fluoroplastic resin by heating at a temperature higher than the melting point of the fluoroplastic resin, the fine particles, which expose themselves at the outer surface of the first part 61, melt to become integral with the surface layer 7. In the case where the first part 61 is heated at a temperature higher than the melting point of the fluoroplastic resin in the form of fine particles, the fine particles expose themselves in the surface of the first part 61 and the particles melt together to become continuous. After that, when the surface layer 7 is formed from a material composed mainly of a fluoroplastic resin in the same way as mentioned above, heating is accomplished at a temperature higher than the melting point of the fluoroplastic resin, so that the fine particles of the fluoroplastic resin, which have joined together and exposed themselves in the surface of the first part 61, melt again to become integral with the surface layer 7.

The fluoroplastic resin in the second part 62' exists in the form of fine particles when heating is accomplished at a temperature like the second temperature for its content to remain uniform (inclusive of generally uniform) across the thickness after heating, so that the fine particles are distributed inside the second part 62'. After that, when the surface layer 7 is formed from a material composed mainly of a fluoroplastic resin, heating is accomplished at a temperature higher than the melting point of the fluoroplastic resin, so that the fine particles distributed inside the second part 62' melt together to become continuous.

In the case of Structure 2 described above, the underlying layer 6 can be formed in the following way.

First, a mixed solution for the first part 61 is prepared from a precursor of the thermosetting resin and the fluoroplastic resin in fine powder form. Another solution for the second part 62' is prepared from a precursor of the thermosetting resin, which is free of the fluoroplastic resin in powder form. The thermosetting resin in the solution for the first part should preferably be the same one as that in the solution for the second part. The solution for the first part is applied to the area of the surface of the core 3 where the first part 61 is to be formed, and the solution for the second part is applied to the area of the surface of the core 3 where the second part 62' is to be formed. This procedure is followed by heating at the first temperature mentioned above.

The guide wire 1 according to the second embodiment produces effects similar to those described above in the first embodiment. In addition, the proximal end 41 of the distal covering layer 4 is much more resistant to peeling, and exhibits improved reliability.

Figure 4:
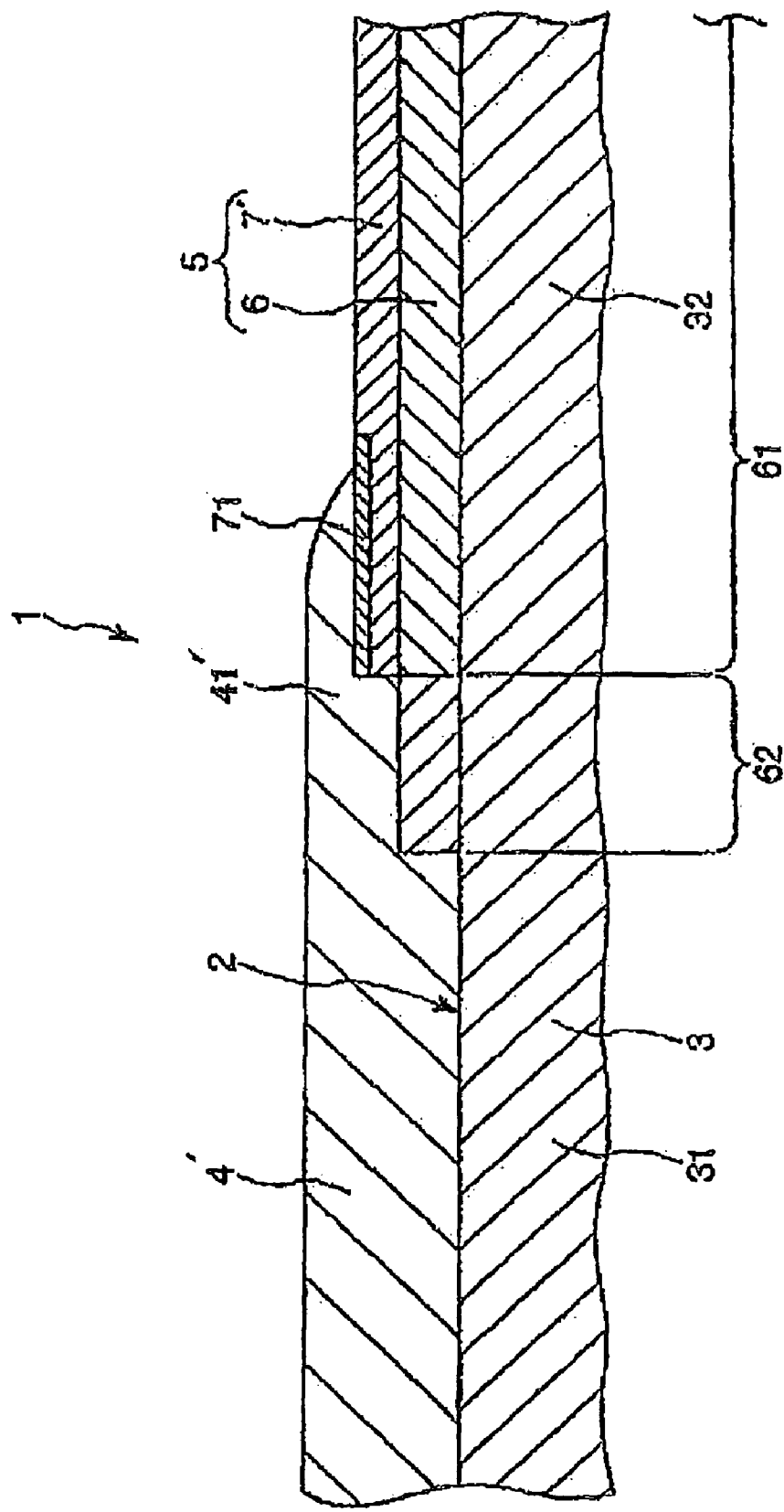
FIG. 4 is an enlarged longitudinal cross-sectional view of a portion of a guide wire according to a third embodiment disclosed here.

FIG. 4 illustrates a second embodiment of the guide wire. In the following description of this embodiment, the phrase "proximal end" refers to the right side in FIG. 4, the phrase "distal end" refers to the left side in FIG. 4, the term "up" refers to the upper side in FIG. 4, and the term "down" refers to the lower side in FIG. 4.

The description below primarily describes differences between this third embodiment of the guide wire and the second embodiment described above. Features in this third embodiment which are the same as those described above are identified by a common reference numeral and a description of such features is not repeated.

The third embodiment is identical to the second embodiment except for the structure of the surface layer 7' and the way in which the distal covering layer 4' overlaps the proximal covering layer 5.

That is, the guide wire 1 shown in FIG. 4 according to the third embodiment is constructed such that the outer surface portion of the distal end of the surface layer 7' is surface-treated to improve adhesion to the distal covering layer 4'. That is, the surface layer 7' includes a surface-treated part 71. The surface-treated part 71 is formed on the entire outer periphery of the distal end of the surface layer 7, meaning the surface-treated part 71 extends around the entire circumference of the distal end of the surface layer 7'. The surface-treated part 71 may also be formed to extend around less than the entire circumference of the outer periphery of the distal end of the surface layer 7'.

Moreover, the proximal end 41' of the distal covering layer 4' overlaps with and tightly adheres to (contacts) the entire outer surface of the second part 62, and it also overlaps with and tightly adheres to (contacts) the outer surface of the surface layer 7', specifically the outer surface of the surface-treated part 71 of the surface layer 7'.

Thus, the proximal end 41' of the distal covering layer 4' firmly adheres to both the outer surface of the second part 62 of the proximal covering layer 5 and the outer surface of the surface-treated part 71.

The surface-treated part 71 may be formed in any appropriate manner. Alternatively, surface treatment may be performed in any appropriate manner on the outer surface of the distal end of the surface layer 7' so long as it improves adhesion to the distal covering layer 4'. Physical or chemical surface treatment, or a combination of physical and chemical surface treatments, is acceptable. Typical treatments include treatment with plasma and treatment with metallic sodium in solution form.

The surface treatment mentioned above gives minute irregularities to the surface of the surface layer 7' and also gives rise to carbonyl groups. The former produces the anchoring effect and the latter induces hydrogen bonds, thereby improving adhesion to the distal covering layer 4'.

This guide wire 1 according to the third embodiment produces effects similar to those of the guide wire according to the second embodiment.

A guide wire is disclosed here by way of several illustrated and described embodiments. However, the present invention is not limited to the illustrated embodiments. Structural aspects of the guide wires may be replaced by features which perform a substantially similar function, and the guide wires can be modified to include additional structure.

In addition, it is within the disclosure here to combine features or aspects of different embodiments in a common guide wire.

Also, the embodiments of the guide wire disclosed here may have a coil of single wire in spiral form encircling the outer periphery of the distal end part 31 of the core 3.

The detailed description above describes various embodiments of a guide wire. However it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A guide wire comprising:
a core comprised of a proximal end part and a distal end part;
a distal covering layer contacting and circumferentially surrounding the distal end part of the core, the distal covering layer possessing a distal end and a proximal end;
a proximal covering layer circumferentially surrounding the proximal end part of the core;
the proximal covering layer comprising a first layer and a second layer, the first layer possessing an outer surface and extending longitudinally over a longitudinal extent;
the first layer contacting and circumferentially surrounding an outer surface of the core, the second layer contacting and circumferentially surrounding an outer surface of a first part of the first layer, the second layer contacting and circumferentially surrounding less than an entirety of the longitudinal extent of the outer surface of the first layer so that a distal end portion of the first layer extends in the distal direction beyond a distal end of the second layer, an outer surface of the distal end portion of the first layer being not covered by the second layer;
the distal covering layer possessing a proximal end portion, the proximal end portion of the distal covering layer contacting and covering at least a part of an outer surface of the distal end portion of the first layer; and
wherein the second layer is formed from a first resin, the first layer is formed from a material containing a thermosetting resin and the first resin, and a content rate of the first resin in the second layer is higher than a content rate of the first resin the first layer, whereby the first layer exhibits stronger adhesive characteristics than the second layer relative to material forming the core and exhibits stronger adhesive characteristics than the core relative to material forming the second layer.

2. The guide wire as defined in claim 1, wherein the distal covering layer possesses a proximal-most end longitudinally spaced from a distal-most end of the second layer so that a gap exists between the proximal-most end of the distal covering layer and the distal-most end of the second layer.

3. The guide wire as defined in claim 1, wherein the first layer is configured so that the outer surface of the first part of the first layer exhibits stronger adhesive characteristics relative to material forming the second layer than the outer surface of the distal end portion of the first layer.

4. The guide wire as defined in claim 1, wherein the first layer is configured so that the outer surface of the distal end portion of the first layer exhibits stronger adhesive characteristics relative to material forming the distal covering layer than the outer surface of the first part of the first layer.

5. The guide wire as defined in claim 1, wherein the first resin is a composition comprising fluoroplastic resin, the fluoroplastic resin comprising more than 50 wt% of said composition.

6. The guide wire as defined in claim 1, wherein the first part of the first layer is formed from a material comprising a fluoroplastic resin and the thermosetting resin, and a content of the fluoroplastic resin in an outer surface portion of the first part, in wt%, is greater than in an inner surface portion of the first part.

7. The guide wire as defined in claim 1, wherein the distal end portion of the first layer is formed from a material containing a fluoroplastic resin and the thermosetting resin, and a content of the fluoroplastic resin in an outer surface portion of the distal end portion of the first layer, in wt%, is less than in an outer surface portion of the first part of the first layer.

8. The guide wire as defined in claim 1, wherein the proximal end portion of the distal covering layer contacts and circumferentially surrounds an entirety of the outer surface of the distal end portion of the first layer.

9. The guide wire as defined in claim 8, wherein the proximal end portion of the distal covering layer contacts and circumferentially surrounds a distal end portion of the second layer.

10. The guide wire as defined in claim 9, wherein the distal end portion of the second layer that is contacted and circumferentially surrounded by the proximal end portion of the distal covering layer possesses a surface-treated outer surface that increases adhesion characteristics of the distal end portion of the second layer relative to an immediately adjoining portion of the second layer that is not surface-treated.

11. A guide wire comprising:
a core comprised of a proximal end part and a distal end part, the proximal end part possessing a distal end;
the distal end part of the core extending in a distal direction from the distal end of the proximal end part of the core;
a distal covering layer covering the distal end part of the core, the distal covering layer possessing a distal end portion and a proximal end; portion
a proximal covering layer covering the proximal end part of the core;
the proximal covering layer comprising an underlying layer that covers an outer surface of the proximal end part and a surface layer that partly covers an outer surface of the underlying layer;
the underlying layer comprising a first part possessing an outer surface covered by the surface layer, the underlying layer also comprising a second part possessing an outer surface not covered by the surface layer;
an outer surface of the second part is surrounded by the proximal end portion of the distal covering layer which contacts the outer surface of the second part; and wherein the surface layer is formed from a first resin, the underlying layer is formed from a material containing a thermosetting resin and the first resin, and a content rate of the first resin in the surface layer is higher than a content rate of the first resin the underlying layer, whereby the underlying layer exhibits stronger adhesive characteristics than the surface layer relative to material forming the core and exhibits stronger adhesive characteristics than the core relative to material forming the surface layer.

12. The guide wire as defined in claim 11, wherein the underlying layer is configured so that the outer surface of the first part of the underlying layer exhibits stronger adhesive characteristics relative to the first resin forming the surface layer than the outer surface of the second part of the underlying layer.

13. The guide wire as defined in claim 11, wherein the distal covering layer is made of a material, the second part of the underlying layer being configured so that the outer surface of the second part of the underlying layer exhibits stronger adhesive characteristics relative to the material forming the distal covering layer than the outer surface of the first part of the underlying layer.

14. The guide wire as defined in claim 11, wherein the first resin is a composition comprising fluoroplastic resin, the fluoroplastic resin comprising more than 50 wt% of said composition.

15. The guide wire as defined in claim 11, wherein the first part of the underlying layer is formed from a material comprising a fluoroplastic resin and the thermosetting resin, and a content of the fluoroplastic resin in an outer surface portion of the first part is higher than in an inner surface portion of the first part.

16. The guide wire as defined in claim 11, wherein the second part is formed from a material containing a fluoroplastic resin and the thermosetting resin, and a content of the fluoroplastic resin in an outer surface portion of the second part is lower than in an outer surface portion of the first part.

17. The guide wire as defined in claim 11, wherein the proximal end portion of the distal covering layer circumferentially surrounds and contacts the outer surface of a distal end portion of the surface layer.

18. The guide wire as defined in claim 17, wherein the distal end portion of the surface layer that is circumferentially surrounded and contacted by the proximal end portion of the distal covering layer possesses a surface-treated outer surface that increases adhesion characteristics of the distal end portion of the surface layer relative to an immediately adjoining portion of the surface layer that is not surface-treated.

* * * * *